United States Patent
Lee

(10) Patent No.: US 9,484,273 B2
(45) Date of Patent: Nov. 1, 2016

(54) APPARATUS FOR MEASURING IMPURITIES ON WAFER AND METHOD OF MEASURING IMPURITIES ON WAFER

(75) Inventor: Seung Wook Lee, Gyeongbuk (KR)

(73) Assignee: LG SILTRON INC., Gumi-si (KR)

( * ) Notice: Subject to any disclaimer, the term of this patent is extended or adjusted under 35 U.S.C. 154(b) by 1216 days.

(21) Appl. No.: 13/425,677

(22) Filed: Mar. 21, 2012

(65) Prior Publication Data

US 2012/0260750 A1   Oct. 18, 2012

(30) Foreign Application Priority Data

Mar. 21, 2011   (KR) .................. 10-2011-0024738

(51) Int. Cl.
| | |
|---|---|
| *H01L 21/66* | (2006.01) |
| *H01L 21/67* | (2006.01) |
| *G01N 1/32* | (2006.01) |
| *G01N 35/00* | (2006.01) |
| *G01N 1/38* | (2006.01) |
| *G01N 1/40* | (2006.01) |

(52) U.S. Cl.
CPC .............. *H01L 22/12* (2013.01); *H01L 21/67* (2013.01); *H01L 21/6708* (2013.01); *H01L 21/67051* (2013.01); *G01N 1/32* (2013.01); *G01N 1/4044* (2013.01); *G01N 35/0099* (2013.01); *G01N 2001/383* (2013.01)

(58) Field of Classification Search
CPC .............. H01L 21/6708; H01L 21/67051; H01L 22/12; H01L 21/67; G01N 1/32; G01N 1/4044; G01N 2001/0099; G01N 2001/383; G01N 35/0099
See application file for complete search history.

(56) References Cited

U.S. PATENT DOCUMENTS

| | | | | |
|---|---|---|---|---|
| 2004/0131783 A1* | 7/2004 | Lee | ........................... | B08B 7/00 427/352 |
| 2004/0140199 A1* | 7/2004 | Mizohata | .................. | C25D 5/04 204/212 |
| 2004/0163670 A1* | 8/2004 | Ko | ........................... | G01N 1/02 134/2 |
| 2009/0249863 A1* | 10/2009 | Kim | .................. | H01L 21/67126 73/31.07 |
| 2012/0260750 A1* | 10/2012 | Lee | .......................... | H01L 22/12 73/866 |

FOREIGN PATENT DOCUMENTS

| | | |
|---|---|---|
| JP | 10-242228 | 9/1998 |
| JP | 10242228 A * | 9/1998 |

(Continued)

OTHER PUBLICATIONS

Chinese Patent Application No. 201280013923 Office Action dated Jul. 28, 2015.
Korean application No. 10-2011-0024738, Office Action dated Aug. 23, 2012 with references cited from Korea Patent Office related to the subject application. (No English Translation provided).

(Continued)

*Primary Examiner* — Marvin Payen
*Assistant Examiner* — Jeremy Joy
(74) *Attorney, Agent, or Firm* — Lewis Roca Rothgerber Christie LLP

(57) ABSTRACT

Provided are an apparatus for measuring impurities on a wafer and a method of measuring impurities on a wafer. The apparatus includes: a wafer aligning device for aligning a wafer; a loading robot for moving and loading the aligned wafer; a rotation stage for rotating the loaded wafer; a scan robot for holding a natural oxide layer etching solution for the wafer and a metallic impurity recovery solution; and a container for receiving a predetermined etching solution and a recovery solution, wherein the scan robot removes an oxide layer on an edge region of the wafer.

4 Claims, 2 Drawing Sheets

(56) References Cited

FOREIGN PATENT DOCUMENTS

| JP | 2004347543 | | | 12/2004 |
|---|---|---|---|---|
| JP | 2004347543 | A | * | 12/2004 |
| KR | 10-1997-0008450 | | | 2/1997 |
| KR | 10-2002-0074757 | | | 10/2002 |
| KR | 10-2004-0001918 | | | 1/2004 |
| KR | 20040001918 | A | * | 1/2004 |
| KR | 10-2004-0055934 | | | 6/2004 |

OTHER PUBLICATIONS

KR PCT Application No. PCT/KR2012/002030 International Search Report dated Oct. 23, 2012.
Korean Application No. 10-2011-0024738, Notice of Allowance mailed Feb. 27, 2013.
Japanese Office Action (without translation), corresponding Japanese Application No. 2014-501000; dated Feb. 16, 2016 (3 pages).

* cited by examiner

… (1)

APPARATUS FOR MEASURING IMPURITIES ON WAFER AND METHOD OF MEASURING IMPURITIES ON WAFER

CROSS-REFERENCE TO RELATED APPLICATIONS

The present application claims priority under 35 U.S.C. 119 and 35 U.S.C. 365 to Korean Patent Application No. 2011-0024738 (filed on Mar. 21, 2011), which is hereby incorporated by reference in its entirety.

BACKGROUND

The present disclosure relates to an apparatus for measuring impurities on a wafer and a method of measuring impurities on a wafer.

In addition to achieving high integration and miniaturization of a semiconductor device by using a silicon wafer, reducing impurities on the silicon wafer, which drastically deteriorate the semiconductor device, is an important task. Accordingly, analyzing and managing such impurities, especially, metal impurities, are important to manage the quality of a silicon wafer.

According to a related art, a method of measuring metallic impurities on the edge of a silicon wafer includes mounting a wafer in a chamber and introducing hydrofluoric acid vapor into the chamber to remove an oxide layer on an entire surface of the silicon wafer. Then, there is a method of qualitatively and quantitatively analyzing metallic impurities through an inductively coupled plasma mass spectrometer, after immersing the perimeter of the wafer in a solution mixed with hydrogen fluoride, hydrogen peroxide, and hydrochloric acid, and extracting metallic impurities on the perimeter of the wafer while rotating a stage having the wafer mounted.

However, according to a related art, only the edge portion of a silicon wafer needs to be analyzed, but a portion intruding the front and backside surfaces by about 3 mm in addition to the edge of the silicon wafer is analyzed. Accordingly, it is difficult to accurately analyze only the edge portion of the silicon wafer according to the related art.

Moreover, according to a related art, in order to increase a recovery rate of Cu impurity, a mixed solution of hydrofluoric acid, hydrogen peroxide acid and hydrochloric acid is used. However, when hydrochloric acid is used as a recovery solution, because of a material (28Si35Cl) combined with remaining Si on the silicon surface and Cl in hydrochloric acid after an oxide layer on the silicon surface is decomposed, mass interference with 63Cu occurs. Therefore, in inductively coupled plasma mass spectrometry methods, there may be an error in analyzing Cu impurity, which may measure Cu impurity even when there is no Cu impurity.

Additionally, according to a related art, since an oxide layer on an entire wafer surface is removed in order to analyze metallic impurities on the perimeter of the silicon wafer, particles may be easily adsorbed on the front side surface, so that the wafer may not be used as another measurement sample besides a metallic impurity analysis sample.

SUMMARY

Embodiments provide a wafer impurity measuring apparatus and a wafer impurity measuring method, which are capable of qualitatively and quantitatively measuring impurities by selectively extracting the metallic impurities on the edge of a silicon wafer.

Embodiments also provide a wafer impurity measuring apparatus and a wafer impurity measuring method for optimizing a recovery solution.

In one embodiment, an apparatus for measuring impurities on a wafer includes: a wafer aligning device for aligning a wafer; a loading robot for moving and loading the aligned wafer; a rotation stage for rotating the loaded wafer; a scan robot for holding a natural oxide layer etching solution for the wafer and a metallic impurity recovery solution; and a container for receiving a predetermined etching solution and a recovery solution, wherein the scan robot removes an oxide layer on an edge region of the wafer.

In another embodiment, a method of measuring impurities on a wafer includes: aligning a wafer and then loading the wafer on a rotation stage by a loading robot; removing an oxide layer on the edge region of the wafer; collecting metallic impurities on the surface of the wafer edge region having the oxide layer removed, by using a recovery solution; and analyzing the metallic impurities by using the extracted recovery solution.

The details of one or more embodiments are set forth in the accompanying drawings and the description below. Other features will be apparent from the description and drawings, and from the claims.

DETAILED DESCRIPTION OF THE EMBODIMENTS

Reference will now be made in detail to the embodiments of the present disclosure, examples of which are illustrated in the accompanying drawings.

In the descriptions of embodiments, it will be understood that when a layer (or film), a region, a pattern, or a structure is referred to as being 'on/above/over/upper' substrate, each layer (or film), a region, a pad, or patterns, it can be directly on substrate each layer (or film), the region, the pad, or the patterns, or intervening layers may also be present. Further, it will be understood that when a layer is referred to as being 'under/below/lower' each layer (film), the region, the pattern, or the structure, it can be directly under another layer (film), another region, another pad, or another patterns, or one or more intervening layers may also be present. Therefore, meaning thereof should be judged according to the spirit of the present disclosure. The size of each component is exaggerated for description and thus does not entirely reflect an actual size.

Figure 1:
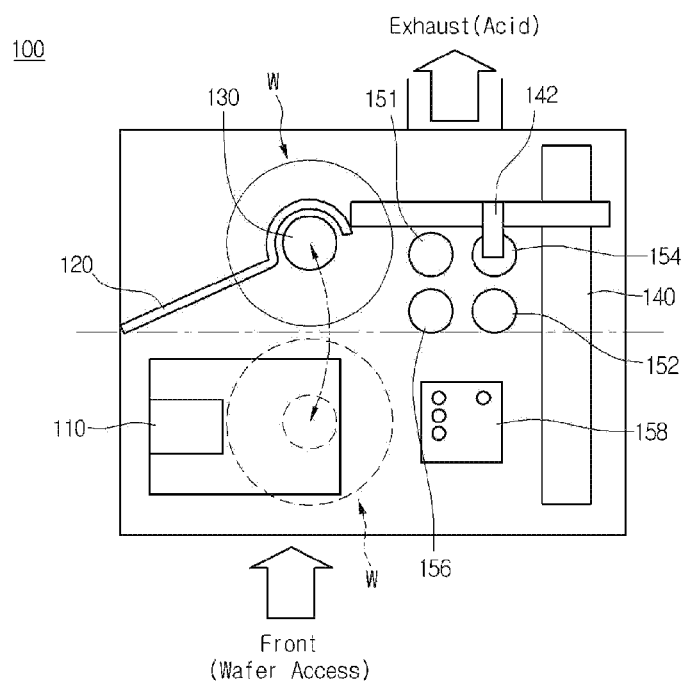
FIG. 1 is a schematic view of an apparatus of measuring impurities on a wafer according to an embodiment.

FIG. 1 is a schematic view of a wafer impurity measuring apparatus 100 according to an embodiment.

The wafer impurity measuring apparatus 100 includes a wafer alignment device 110 for aligning a wafer W, a loading robot 120 for moving the aligned wafer, a rotation stage 130 for rotating the loaded wafer, a scan robot 140 for holding a natural oxide etching solution to the wafer and a metallic impurity recovery solution, and a first container 151 and a second container for receiving a predetermined etching solution and a recovery solution.

The scan robot 140 may move in three-axes (i.e., x-y-z directions).

The scan robot 140 may remove an oxide layer on the wafer edge region.

Additionally, the scan robot 140 may collect metallic impurity on the surface of the wafer edge region having the oxide layer removed, by using the recovery solution.

For example, the scan robot 140 further includes a tube 142 disposed at the bottom end thereof and holding the etching solution and the recovery solution, and the bottom of the tube 142 may have a diagonally-cut shape.

Additionally, the cut region in the bottom end of the tube 142 may be disposed on the lateral side of the wafer edge region.

For example, the recovery solution S (refer to FIG. 3) contacts the wafer edge region in order to collect metallic impurity on the wafer edge region according to an embodiment. At this point, the shape of the tube 142 holding the recovery solution S is important.

Apparatus consistent with the present disclosure may include a tube disposed at the bottom end of the scan robot that may hold the etching solution or the recovery solution, the bottom of the tube may include a diagonally-cut shape, since the scan robot 140 is disposed above the wafer, if the tube 142 is manufactured being diagonally cut and holds the recovery solution thereon, the recovery solution S contacts substantially only the wafer edge region. If the rotation stage 130 rotates in such a state, metallic impurities on the wafer edge may be collected. The metallic impurities may be quantitatively or qualitatively analyzed through an inductively coupled plasma mass spectrometer by using the collected recovery solution.

The wafer impurity measuring apparatus 100 may include a third container 154 and a fourth container 156 for cleaning the tube 142 of the scan robot 140 and may include a vial tray 158 for containing a sample. The third container 154 may contain a deionized water (DIW) rinse, and the fourth container 156 may contain a chemical rinse, but the present invention is not limited thereto.

Apparatus and methods consistent with the present disclosure may selectively extract metallic impurities on the silicon wafer edge region for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Hereinafter, a method of measuring impurities on a wafer will be described according to an embodiment with reference to FIGS. 1 to 3.

First, the wafer W is aligned, and loaded into on the rotation stage 130 by the loading robot 120.

Figure 2:
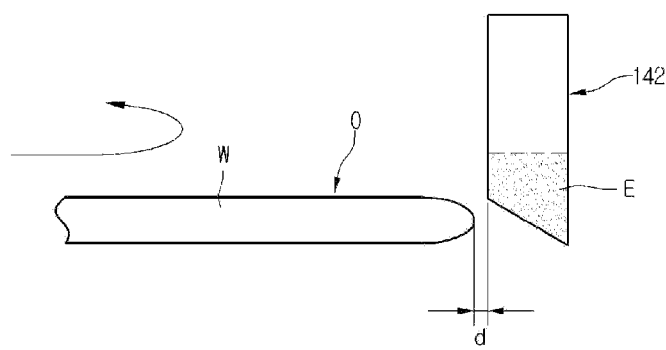
FIG. 2 is a view of when an oxide layer on a wafer edge region being removed according to a method of measuring impurities on a wafer according to an embodiment.

Then, as shown in FIG. 2, the natural oxide layer O on the edge region of the wafer W is removed.

For example, the removing of the oxide layer O on the edge region of the wafer W may include approaching toward the edge region of the wafer W when the scan robot 140 collects and holds an etching solution E, and rotating the rotation stage 130 having the wafer W mounted, not contacting the wafer edge region and being spaced for a predetermined distance d.

The etching solution E may be hydrofluoric acid (HF) but is not limited thereto.

When the natural oxide layer on the wafer edge region is selectively removed using the property that the etching solution E is volatilized at a room temperature, the distance d between the wafer edge region and the tube may be less than about 1 mm, but is not limited thereto. If vaporized etching solution is supplied with the pressure of a predetermined supply device, the distance may be more than and equal to about 1 mm.

An amount of the etching solution E that the scan robot 140 collects and holds is $100\ \mu L \leq V1 \leq 1000\ \mu L$. If an amount of the etching solution E is less than about $100\ \mu L$, the oxide layer may not be sufficiently removed, and if more than about $1000\ \mu L$, the etching solution E may drop.

According to an embodiment, the scan robot 140 includes a tube 142 disposed at the bottom end thereof and holding an etching solution or a recovery solution, and the bottom of the tube 142 may have a diagonally-cut shape.

Additionally, the cut region in the bottom end of the tube 142 may be disposed on the lateral side of the wafer edge region.

After the natural oxide layer O on the wafer edge region is removed, remaining hydrofluoric acid (HF) in the tube 142 of the scan robot 140 may be dumped into a drain, and the tube 142 may be cleaned using DIW in the third container 154.

Figure 3:
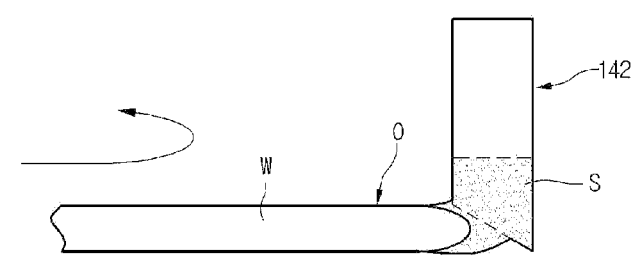
FIG. 3 is a view of when metallic impurities are collected using a recovery solution according to a method of measuring impurities on a wafer according to an embodiment.

Next, as shown in FIG. 3, the metallic impurity on the surface of the wafer edge region having the oxide layer O removed is collected by using the recovery solution S.

For example, the collecting of the metallic impurity on the surface of the wafer edge region by using the recovery solution may include supplying the recovery solution S by using the scan robot 140 and contacting the recovery solution S on the wafer edge region, and extracting the metallic impurity on the wafer edge region by rotating the rotation stage 130.

An amount of the recovery solution S that the scan robot 140 collects and holds is $100\ \mu L \leq V2 \leq 1000\ \mu L$. If an amount V2 of the recovery solution is less than about $100\ \mu L$, there is a disadvantage that the number of measurable metallic elements become smaller, and if more than about $1000\ \mu L$, a sample volume becomes larger, so that a detectability for a low concentration impurity may be low.

According to an embodiment, the tube 142 disposed at the bottom end of the scan robot 142 holds an etching solution and the bottom of the tube 142 may have a diagonally-cut shape.

For example, the recovery solution S (refer to FIG. 3) contacts the wafer edge region in order to collect metallic impurity on the wafer edge region according to an embodiment. At this point, the shape of the tube 142 holding the recovery solution S is important.

Apparatus consistent with the present disclosure may include a tube disposed at the bottom end of the scan robot that may hold the etching solution or the recovery solution, the bottom of the tube may include a diagonally-cut shape, since the scan robot 140 is disposed above the wafer, if the tube 142 is manufactured being diagonally cut and holds the recovery solution thereon, the recovery solution S contacts substantially only the wafer edge region.

If the rotation stage 130 rotates in such a state, metallic impurities on the wafer edge may be collected. The metallic impurities may be quantitatively or qualitatively analyzed through an inductively coupled plasma mass spectrometer by using the collected recovery solution.

Moreover, unlike that a mixed solution of hydrofluoric acid, hydrogen peroxide and hydrochloric acid is used as a recovery solution according to a related art, the recovery solution S according to an embodiment may improve a Cu recovery rate by using a mixed solution of hydrofluoric acid and hydrogen peroxide.

In order to improve a recovery rate, the recovery solution may have the chemical composition of $X\%HFY\%H_2O_2$ ($0.1 \leq X \leq 5$, $1 \leq Y \leq 28$).

If the composition of HF and $H_2O_2$ is less than the composition range, recovery is poor, and if it is more than the composition range, interference of an Inductively Coupled Plasma/Mass Spectrometer (ICP/MS) may occur and thus accurate measurement may not be obtained.

If the mixed solution of hydrofluoric acid and hydrogen peroxide is used as the recovery solution S, mass interference of 28Si35Cl and 63Cu described above as the disadvantage of the related art may be prevented so that analysis errors may be prevented.

According to the wafer impurity measuring apparatus and the wafer impurity measuring method, metallic impurities on the silicon wafer edge region are selectively extracted for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Figure 4:
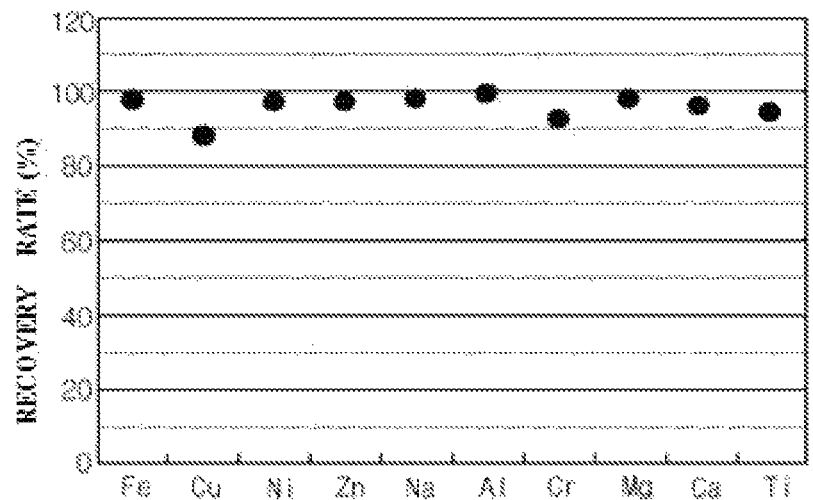
FIG. 4 is a view illustrating a recovery rate of metallic impurities on s wafer edge region when a method of measuring impurities on a wafer according to an embodiment is applied.

FIG. 4 is a view illustrating a recovery rate of metallic impurity measurement on silicon wafer edge region when a method of measuring impurities on a wafer is applied according to an embodiment.

In order to measure a recovery rate of a wafer edge region, if the wafer surface is contaminated through a spin coating method, the wafer edge region in addition to the wafer surface is naturally contaminated during rotation.

Moreover, if the metallic impurities on the front side of the wafer are removed through a VPD/ICP-MS method, the wafer having only the wafer edge region contaminated may be manufactured.

Figure 5:
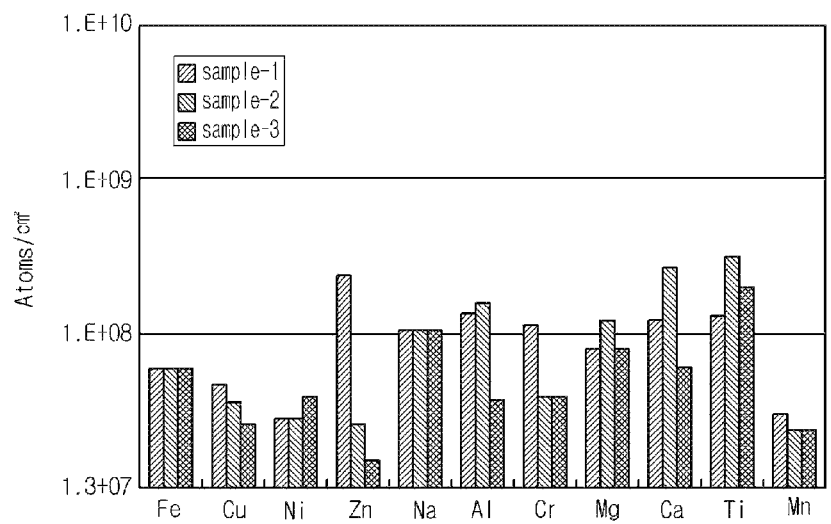
FIG. 5 is a view illustrating measurement results of metallic impurities on a wafer after impurities on a wafer edge region are measured when a method of measuring impurities on a wafer according to an embodiment is applied.

This wafer is repeatedly measured one time, two times, and three times, and a recovery rate is calculated using the equation of [1−(one time measurement concentration/two times measurement concentration)×100]. FIG. 5 shows a result of a recovery rate and the recovery rate of metallic impurity is more than or equal to about 88%. Accordingly, reliability of measurement results of the present invention is excellent.

FIG. 5 is a view illustrating sample results of metallic impurity measurements (Sample-1, Sample-2, Sample-3) on the wafer side after measuring impurities on the wafer edge region when a method of measuring impurities on a wafer according to an embodiment is applied.

According to an embodiment, a natural oxide layer on the front side and back side of the silicon wafer is not damaged, so that the silicon wafer may be used for another measurement after analysis. For example, as shown in FIG. 5, after measuring metallic impurity on the wafer edge region, the metallic impurities on the front side is measured. As a result, the metallic contamination is less than 5E8 atoms/cm$^2$. Therefore, the wafer may be used for Bulk Fe, direct surface oxide defect (DSOD), and thermal treatment evaluations besides the surface metallic impurity evaluation.

Apparatus and methods consistent with the present disclosure may selectively extract metallic impurities on the silicon wafer edge region for a quantitative and qualitative analysis.

Additionally, according to an embodiment, only the natural oxide layer on the wafer edge region is removed, the natural oxide layer on the front side and back side surfaces is not damaged, and also impurities may be minimized, so that the wafer after this measurement may be used as another measurement sample.

Furthermore, according to an embodiment, a recovery rate of impurities may be increased and the mass nesting phenomenon of a mass spectrometer may be resolved by optimizing a recovery solution so that analysis errors may be prevented.

Although embodiments have been described with reference to a number of illustrative embodiments thereof, it should be understood that numerous other modifications and embodiments can be devised by those skilled in the art that will fall within the spirit and scope of the principles of this disclosure.

More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An apparatus for measuring impurities on a wafer, comprising:
   a wafer aligning device for aligning a wafer;
   a loading robot for moving and loading the aligned wafer;
   a rotation stage for rotating the loaded wafer;
   a scan robot for holding a natural oxide layer etching solution for the wafer and a metallic impurity recovery solution; and
   a container for receiving a predetermined etching solution and a recovery solution, wherein the scan robot includes a tube disposed at the bottom end of the scan robot and holding the etching solution and the recovery solution, and the bottom of the tube has a diagonally-cut shape.

2. The apparatus according to claim 1, wherein the tube holds the etching solution to remove an oxide layer on an edge region of the wafer, and a cut region in a bottom end of the tube is disposed on a lateral side of the wafer edge region.

3. The apparatus according to claim 2, wherein the tube holds the recovery solution to collect metallic impurities on a surface of the wafer edge region having the oxide layer removed, and the cut region in the bottom end of the tube is disposed on the lateral side of the wafer edge region.

4. The apparatus according to claim 1, wherein a cut region in a bottom end of the tube is disposed at a lateral side of the wafer edge region.

* * * * *